United States Patent
Greenwood et al.

(10) Patent No.: US 6,877,249 B1
(45) Date of Patent: Apr. 12, 2005

(54) METHOD OF DRYING A LACTULOSE SOLUTION

(75) Inventors: Alan Kenneth Greenwood, Herts (GB); Anthony Christopher Allen, Herts (GB); Jaap Van Dijk, Amersfoort (NL)

(73) Assignee: Relax Limited, Herts (GB)

(*) Notice: Subject to any disclaimer, the term of this patent is extended or adjusted under 35 U.S.C. 154(b) by 0 days.

(21) Appl. No.: 09/857,650

(22) PCT Filed: Dec. 13, 1999

(86) PCT No.: PCT/GB99/04195

§ 371 (c)(1),
(2), (4) Date: Oct. 12, 2001

(87) PCT Pub. No.: WO00/36153

PCT Pub. Date: Jun. 22, 2000

(30) Foreign Application Priority Data

Dec. 11, 1998 (GB) .............................. 9827423

(51) Int. Cl.⁷ .................................. F26B 3/08

(52) U.S. Cl. .............................. 34/361; 34/304; 34/406; 34/496; 127/46.1; 127/65

(58) Field of Search .......................... 34/302, 304, 359, 34/360, 361, 406, 493, 496; 127/42, 46.1, 65

(56) References Cited

U.S. PATENT DOCUMENTS

| | | | | |
|---|---|---|---|---|
| 4,147,773 A | * | 4/1979 | Ogasa | 424/93.4 |
| 5,003,061 A | * | 3/1991 | Carobbi et al. | 536/127 |
| 5,034,064 A | * | 7/1991 | Deya et al. | 127/46.3 |
| 5,415,695 A | * | 5/1995 | Weterings et al. | 127/58 |
| 6,534,087 B2 | * | 3/2003 | Busson et al. | 424/464 |
| 6,723,890 B2 | * | 4/2004 | Tucker et al. | 588/200 |

* cited by examiner

*Primary Examiner*—Denise L. Esquivel
*Assistant Examiner*—Kathryn S. O'Malley
(74) *Attorney, Agent, or Firm*—Hodgson Russ LLP

(57) ABSTRACT

A method of drying a lactulose solution comprises introducing the solution into a vacuum chamber at elevated temperature and at reduced pressure so that the solution forms a foam, drying the foam under reduced pressure, and milling or grinding or breaking the dried foam into powder.

11 Claims, 2 Drawing Sheets

METHOD OF DRYING A LACTULOSE SOLUTION

The present invention relates to a method of drying a solution, in particular to a method of drying a lactulose solution so as to obtain a powder which can be reconstituted with water to form a lactulose solution.

Lactulose is a synthetic disaccharide that consists of fructose and galactose. As there is no corresponding disaccharidase in the human intestinal mucosal cells, lactulose is not split in the small intestine and therefore is not absorbed. In the colon, it is metabolised to organic acids in short chains (acetic and lactic acids) by the gut flora. This fermentation acidifies the content of the intestine and has an osmotic effect; the higher the dose, the stronger the osmotic effect. Hence, lactulose solutions are used as laxatives. Lactulose preparations that are commercially available also include quantities of galactose, lactose, and other sugars.

A problem with lactulose solutions is that they are awkward to transport—typical lactulose solutions contain about 30 percent by water and hence a large amount of weight that is transported is made up of this water. It would be preferable for a powdered or other dry formulation of lactulose to be transported, and hence a number of proposals have been made to dry lactulose solutions. All of these proposals have specific disadvantages.

U.S. Pat. No. 3,716,408 describes a lactulose powder containing 55 percent or above lactulose obtained by spray drying. It is necessary to incorporate an amount of an agent to promote drying of the lactulose, specifically konnyaku powder, into the solution in order for drying to be successful. However, it is highly undesirable for pharmaceutical preparations to include any such additional agents.

U.S. Pat. No. 5,326,405 describes a method for preparation of crystal-water-free lactulose by simultaneous stirring and heating of a lactulose solution to reduce its water content and introduction of seed crystals until a free-flowing powder is obtained. A disadvantage of this method is that it needs to be carried out in batches and is not suitable for commercial scale production. Additionally, there is the need to introduce seed crystals and these crystals may contaminate or be different form the content of the lactulose solution, as well as introducing a further step into the process.

U.S. Pat. No. 5,415,695 describes a further method of preparing solid forms of lactulose by evaporating lactulose syrup to reduce its water content and then cooling the evaporated syrup until it solidifies. The solidified product can then be milled into powder. The method is preferably carried out with very rapid cooling of the lactulose solution. This often results in a product that needs extensive milling or other processing to obtain a uniform powder. Further, it is not possible to carry out this process in a continuous fashion.

A still further process for manufacturing solid lactulose preparations is described in WO 98/19684. An aqueous lactulose solution is spray-dried in a countercurrent of air into a fluidised bed container. However, to obtain reliable output of dried lactulose it is generally necessary for a swelling or gelling agent to be included to absorb water from the lactulose solution. As previously mentioned, the presence of any such agent is highly undesirable in pharmaceutical preparations containing lactulose.

JP49-54556 describes a method for drying lactulose syrup in a shelf-type freeze dryer at temperatures of >−45° C. under reduced pressure. In this process, a batch of lactulose is spread onto a tray, freeze-dried to 80–85% solids, and then warmed gradually to form a foam, which is dried under reduced pressure at a temperature of 80° C. for 4 hours, followed by a temperature of 35° C. for 18 hours. This process requires long drying times and is only suitable as a batch operation.

It is an object of the present invention to provide an alternative method for drying of lactulose solutions so as to obtain a powdered form of lactulose.

It is a further object of the present invention to provide a method of drying lactulose which does not require the presence of agents such as swelling or drying agents or seed crystals.

Accordingly, a first aspect of the present invention provides a method of drying a lactulose solution comprising introducing the solution into a vacuum chamber at elevated temperature and at reduced pressure so that the solution forms a foam, and drying the foam to obtain a dried lactulose-containing composition.

It has advantageously been found that the foam obtained can be dried, typically under reduced pressure, to obtain a powdered form of lactulose without the need for swelling or drying agents and without the need for seed crystals. Thus, the lactulose powder obtained by the method of the invention is eminently suitable for pharmaceutical compositions, and is suitable for reconstitution with water to provide a lactulose solution.

The dried product obtained using the invention has a number of advantages. It is lighter than the currently available syrup and easier to measure in accurate doses. Bottles of syrup are liable to break, whereas packets of powder avoid this problem. The powder can be reconstituted with tap water to provide a dosage solution—10 to 15 g in a cap of water, about 200 ml, is typical.

In an example of use of the invention, a lactulose solution having at least 80 percent solids by weight is introduced into a vacuum chamber at elevated temperature and at reduced pressure so that the solution forms a foam. This foam is dried under reduced pressure and a powder then obtained by milling or grinding or breaking the dried foam. The resultant powder typically has a moisture content of less than 10% and preferably less than 8%, most preferably less than 6%, and is in the form of a white, granular powder that is free flowing and can be packaged directly without further treatment. Upon reconstitution with water the powder forms a lactulose solution.

Prior to drying, the lactulose solution is suitably maintained outside the vacuum chamber at about atmospheric pressure and ambient temperature. Solution is then fed into the vacuum chamber and upon encountering conditions of elevated temperature and reduced pressure within the chamber expands into a foam. In this foam the profusion of bubbles that are created means that compared to the solution a very large surface area is presented to the environment inside the vacuum chamber and the lactulose solution has been spread out into a large number of thin films that make up the bubbles and other parts of the foam; the solution has thus been converted into a form suitable for drying.

In the method of the invention, the highest temperature is generally at the point of entry into the chamber and the method comprises extruding the solution through a nozzle so that the solution foams as it exits the nozzle and enters the environment of the chamber. The invention is suited to be carried out continuously and in an embodiment of the invention the drying is carried out using a moving belt onto which is deposited the lactulose foam exiting from the nozzle. The belt moves forwards, away from the nozzle, so creating space for further foam that continues to exit from the nozzle. In a specific embodiment of the invention, as the belt moves forwards so the nozzle moves back and forth across the belt covering a portion of or the whole of the width of the belt with foam. By the time the nozzle has travelled from one side to the other and returned the belt has advanced sufficiently to provide space for a further line of foam to be deposited. Thus, most preferably, the method is carried out in a vacuum belt dryer and comprises evenly distributing the solution over the belt of the dryer as the belt is moved. A non-stick coating on the belt, such as a Teflon coating is preferred, for ease of removing dried foam further along the belt.

Drying can be carried out at varying or fixed temperatures. The drying temperature may rise from one section of the chamber to the next and then fall. The temperature may be chosen so that the solution does not initially foam an entry into the chamber but does so when advanced to a higher temperature zone. Preferably the highest temperature is at or about the point of entry of solution into the chamber. It is further preferred that the foam is dried at a temperature which is reduced cover time. Initially, when the foam is first formed at high temperature, if the temperature were to be reduced too quickly the foam might collapse. The temperature is thus kept fairly high for at least the first section of the drying stage to maintain the foam. As the water content is reduced so the foam solidifies and the temperature can be reduced in latter stages of drying. This staged temperature drop has the advantage that the risk of damage to the lactulose caused by excessive heating is substantially avoided. A further advantage is that the final stage can be chosen to be at a temperature that is at or close to ambient, whereby dried lactulose exiting the dryer can immediately be packaged and sealed, for example in plastic bags that might not be suitable to receive hot lactulose.

The method of the invention preferably comprises passing the foam through a plurality of drying zones, each zone being at a different temperature, the temperature of the zones reducing from one zone to the next. Foaming of the solution occurs when the combination of temperature and pressure is such that bubbles of steam form from the water content of the solution.

The method can advantageously comprise passing the foam through a first zone at a temperature of at least 100° C. and passing the foam through a final zone at a temperature of 50° C. or less. The foam may suitably reside in each zone for at least 3 minutes. More specifically, the method may comprise passing the foam through a first zone at a temperature of about 110–130° C. for a period of about 3–12 minutes, passing the foam through a second zone at a temperature of about 70–90° C. for a period of about 3–12 minutes and passing the foam through a third zone at a temperature of about 20–40° C. for about 3–12 minutes. The time in each zone is more preferably 4–6 minutes.

Whilst the temperature can readily be changed from one zone to the next in a vacuum chamber, it is usually technically more difficult to provide zones of differing pressure. In the method of the invention, the pressure in the vacuum chamber is usually maintained below 50 mbar, and preferably below 40 mbar and above 5 mbar. To provide the conditions suitable for foaming of the solution a combination of temperature and pressure is needed, and at below 50 mbar a temperature of at least 100° C. has been found to produce a good foam with at least 110° C. generally being used. A lower temperature may also be effective, dependent upon the chamber pressure. Higher temperatures may also be used provided these are not so high as to risk caramelization or other detriment to the lactulose. Generally, with chamber pressures in the range 5–50 mbar temperature of 100–150° C. are suitable to produce the foaming of the solution needed for satisfactory drying, though it is the combination of temperature and pressure that is used rather than any particular value of either. Reduced pressure can be any pressure below atmospheric.

The invention further provides a method of drying a lactulose solution comprising subjecting the solution to conditions of raised temperature and reduced pressure so that the solution expands into a foam, and drying the foam thereby produced.

In a second aspect of the present invention there is provided a method of drying a lactulose solution by spreading out the solution into a thin film, and drying the film under reduced pressure. The film should preferably have a thickness of no more than 2 mm. Thus, the method comprises forming substantially continuous thin sheets 2 mm or less thick of the lactulose solution. These can be dried at reduced pressure without needing seed crystals or agents to help absorb water from the lactulose solution.

The methods of the invention are suitable for drying of lactulose-containing solutions having varying lactulose compositions. Generally, lactulose-containing solutions contain at least about 40% lactulose by weight, typically around 50 percent or more. High water content solutions can be dried, though when the water content of the solution is high this means the height of foam produced in the method is increased and this can produce impractical levels of foam in some dryers, for example if there is limited headspace above the belt. Solutions with 60 or more percent solids by weight can be dried by the present method. Good results have been obtained using the method of the invention to dry a lactulose solution having 80 percent by weight solids or more preferably at least 82 percent, made up of a combination of lactulose and optionally other sugars such as galactose, lactose, tagatose, fructose and epilactose of which the major component is lactulose. In a specific embodiment of the invention, a lactulose solution comprises 69 percent solids by weight, made up of 50 percent lactulose, 4 percent galactose, 4 percent lactose, 2 percent tagatose, 1 percent fructose, 3 percent epilactose and 5 percent other sugars. The solids content of this solution is then reduced, such as by evaporation of water at elevated temperature, to obtain a solution having at least 80 percent solids by weight, and this solution has produced good results in specific embodiments of the invention, leading to a dried product that is white and free-flowing and is readily reconstituted with water to form a lactulose solution.

The invention yet further provides, in an additional aspect, a method of drying a sugar-containing solution, comprising introducing the solution into a vacuum chamber at elevated temperature and at reduced pressure so that the sugar-containing solution forms a foam, and drying the foam under reduced pressure. Optionally, the dried foam can be milled or ground or broken into powder. Other referred features and embodiments of the this further aspect of the invention correspond to the preferred features and embodiments of the first aspect of the invention.

There now follows a description of specific embodiment of the invention, illustrated by the accompanying drawings in which.

Figure 1:
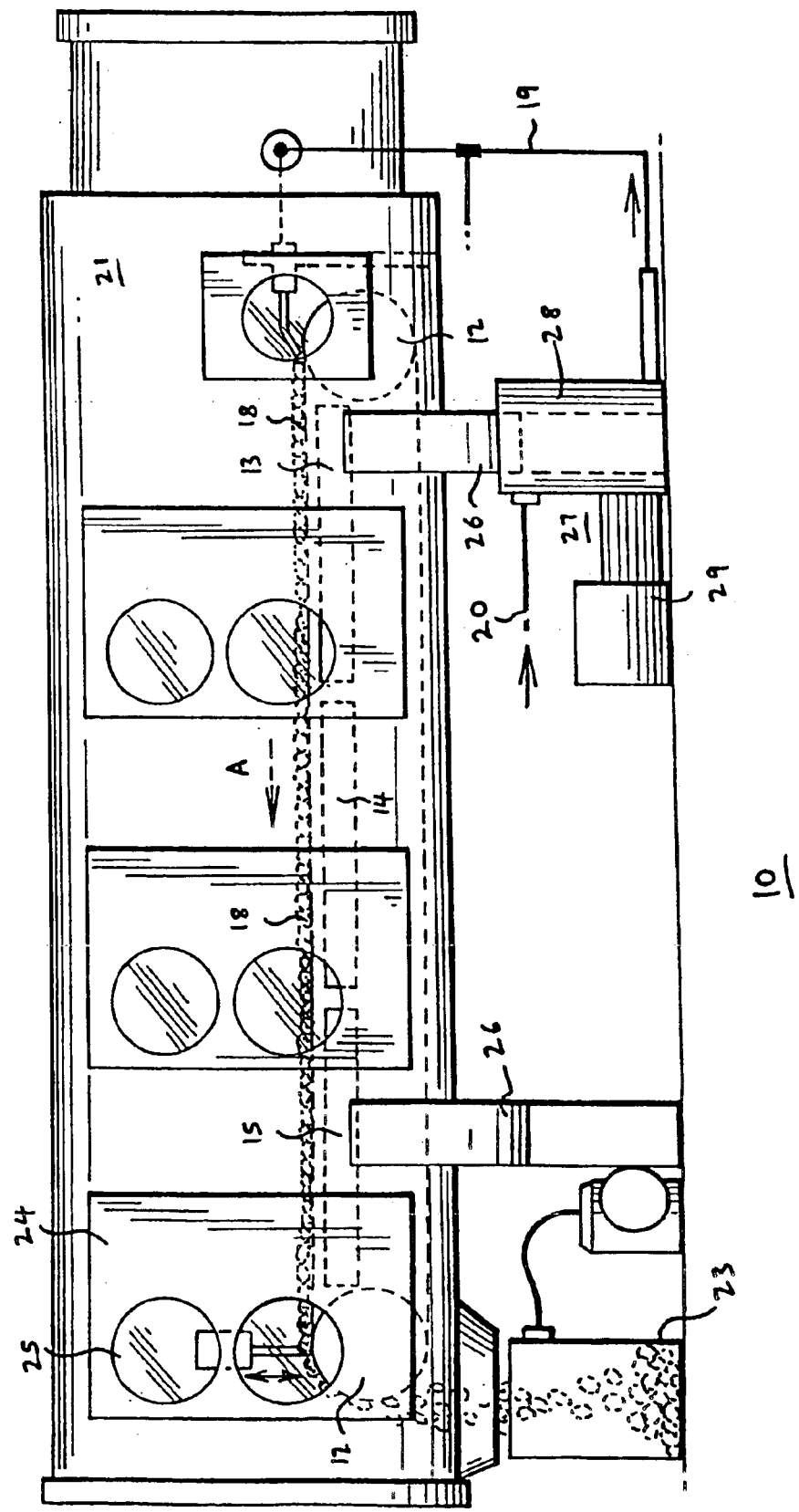
FIG. 1 shows a schematic side view of apparatus for carrying out the present invention.
Figure 2:
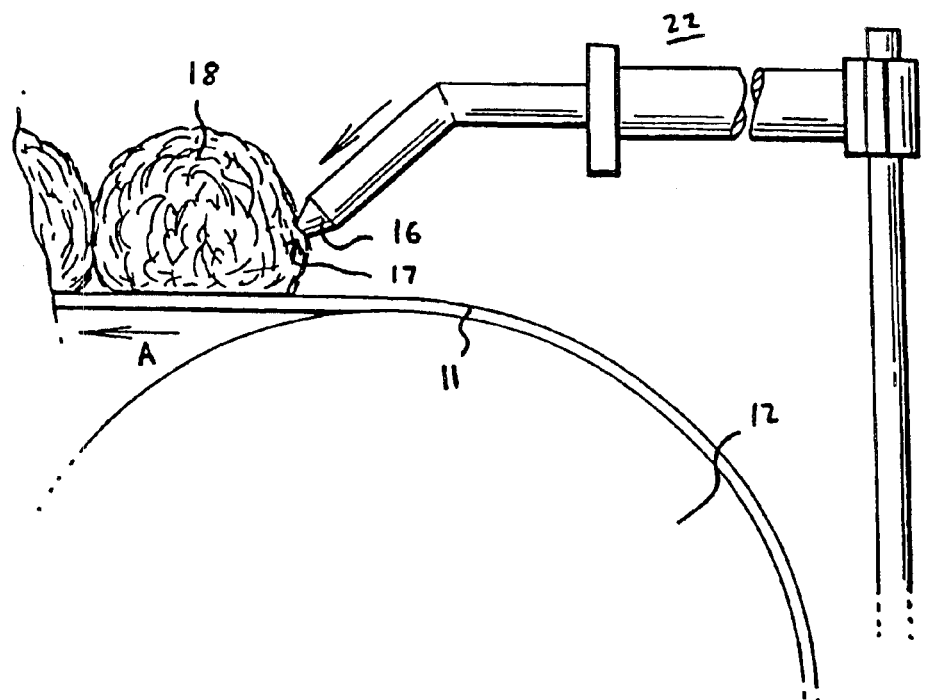
FIG. 2 shows an enlarged view of a dispenser head.
Figure 3:
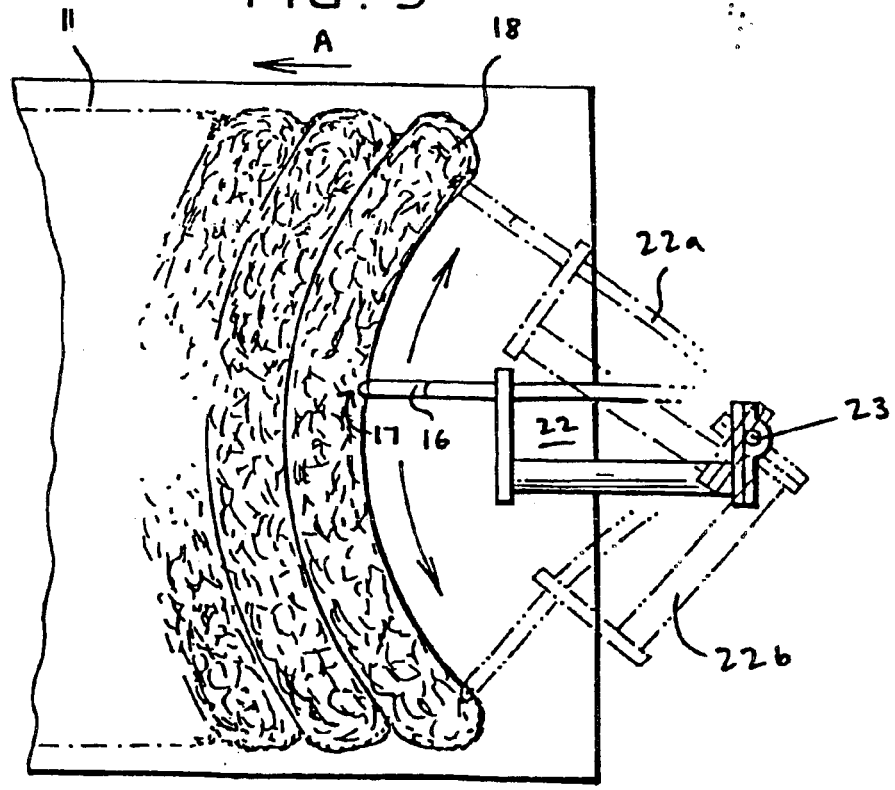
FIG. 3 shows a view from above the dispenser head of FIG. 2.

Referring to FIGS. 1, 2 and 3 apparatus 10 comprises a moving Teflon-coated belt 11 mounted on rollers 12 for movement in the direction shown by the arrow A. First, second and third heaters 13, 14 and 15 are located immediately underneath the belt 11 and linked to control apparatus (not shown) for maintaining the first, second and third heating zones in the immediate vicinity of the respective heaters at different temperatures. Heating is achieved using hot water or steam. Thermal oils may also be used. In the vacuum environment of the chamber, heating is achieved by conduction and radiation, and the heaters are very close to or in contact with the belt.

A lactulose solution is introduced into the apparatus via nozzle 16 at the end of a fluid line 19 connected to the lactulose solution which is located externally of the apparatus and connected to fluid input 20. Arrows indicate the direction of flow of solution. The nozzle, belt and heating zones are all located within a vacuum chamber 21 of the apparatus. The nozzle moves in a reciprocating motion at the end of a dispenser head 22 mounted on pivot 23 moving back and forth across the belt as the belt moves forwards, depositing an even layer of solution over virtually the whole of the width of the belt. Outlines 22a and 22b show the extent of travel of the dispenser head 22 in operation.

Referring in more detail to FIG. 1, lactulose solution is extruded from exit point 17 of the nozzle 16 and upon entry into the vacuum chamber, under conditions of elevated temperature and reduced pressure, expands into foam 18. The exit point 17 has a diameter of about 5 mm and at a temperature of about 120° C. and a pressure of 50 mbar or less a foam is produced which typically has a height of around 40–70 mm.

The belt 11 moves slowly in the direction shown by arrow A and the belt speed is such that when the nozzle has completed its return trip from one side of the belt to the other and back the belt has advanced by an amount equal to the width of foam produced by the extruded solution. As a result a foam carpet is laid down on the belt and the extrusion and drying is continuous. The foam dries as it is moved by the belt through the various heating zones under reduced pressure. The first zone is at about 120° C. and the last at about 40° C., with intermediate zones at intermediate temperatures.

Dried foam at about 40° C. then falls off or is cut off the end of the belt and falls into a collecting bin 23. The dried foam is optionally subjected to milling or grinding or other breaking to obtain a lactulose powder.

The apparatus also has inspection covers 24 and inspection ports 25 along its side and is supported by legs 26. Fluid feed apparatus 27 comprises a container 28 for holding the solution and motor plus gearbox 29 for pumping the solution along fluid line 19.

EXAMPLE 1

A lactulose-containing solution was prepared having 80 percent by weight solids of which about 70 percent was lactulose. This solution was introduced into the vacuum chamber of the apparatus as described above with reference to the drawings through a nozzle of 5 mm diameter and into a heating zone at a temperature of about 120° C. The pressure in the vacuum chamber was maintained at about 30 mbar. The three heating zones in the apparatus were maintained at about 120° C., about 80° C. and about 40° C., with a belt speed such that the foam remained within each area for about 10 minutes.

The lactulose solution introduced into the chamber expanded into a foam of about 50 mm height having a yellowy-white colour and a glistening appearance. On exiting from the third heating zone, at about 40° C., the foam had dried to a moisture content of about 4 percent and was broken up into a free-flowing powder. This powder was suitable for direct packaging into plastic bags or other containers and was found upon simple mixing with water readily to be reconstituted into a lactulose-containing solution.

EXAMPLE 2

The method of Example 1 was repeated with variations in the solids content of the lactulose solution, the temperatures in the individual heating zones, the pressure within the vacuum chamber and the belt speed (i.e. the total residence time in all heating zones) and with the feeding time and temperatures recorded.

The specific conditions and results obtained are shown in the following tables, and the examples were carried out using apparatus having four individual heating zones.

TABLE 1

| Test No. | 1 | 2 | 3 | 4 |
|---|---|---|---|---|
| Solids content of lactulose solution, % | 84 | 84 | 84 | 84 |
| Temperatures in zones 1–4, ° C. | 120/100/80/40 | 80/120/80/40 | 80/100/80/40 | 80/100/80/40 |
| Vacuum abs, mbar | 25 | 35 | 35 | 10 |
| Residence time, min | 42 | 42 | 42 | 18 |
| Feed temperature, ° C. | 36 | 35 | 35 | 37 |
| Feeding time, min | 6 | 6 | 6 | 6 |
| Dried Product Quantity, Kg | 0.6255 | 0.5978 | 0.6622 | 0.6744 |
| Output, Kg/m²/h | 3.91 | 3.74 | 4.14 | 4.22 |
| Colour | white | white | white | white |
| Residual moisture, % | 3.0 | 1.9 | 4.4 | 4.2 |

TABLE 2

| Test No. | 5 | 6 | 7 | 8 |
|---|---|---|---|---|
| Solids content of lactulose solution, % | 84 | 84 | 84 | 84 |
| Temperatures in zones 1–4, ° C. | 120/100/80/22 | 120/100/80/22 | 120/100/80/23 | 140/120/100/40 |
| Vacuum abs, mbar | 10 | 10 | 10 | 10 |
| Residence time, min | 18 | 18 | 18 | 19 |
| Feed temperature, ° C. | 37 | 38 | 38 | 38 |
| Feeding time, min | 6 | 6 | 3 | 6 |
| Dried Product Quantity, Kg | 0.6669 | 0.6733 | 0.3793 | 0.6784 |
| Output, Kg/m²/h | 4.17 | 4.21 | 4.74 | 4.24 |
| Colour | white | white | white | white |
| Residual moisture, % | 4.4 | 5.0 | 5.5 | 3.5 |

The invention thus provides a method for drying a lactulose solution into a powdered form, without the need for swelling or gelling agents or seed crystals, and also provides a powdered form of lactulose that is readily reconstituted with water to reform a lactulose solution.

What is claimed is:

1. A method of drying a lactulose solution, comprising introducing the solution into a vacuum chamber at elevated temperature and at reduced pressure so that the solution forms a foam;

drying the foam under reduced pressure; and optionally, subjecting the dried foam to a process selected from the group consisting of milling, grinding, breaking and combinations thereof to form a powder.

2. A method according to claim 1 comprising extruding the solution through a nozzle so that the solution foams as it exits the nozzle.

3. A method according to claim 1, wherein the foam is dried at a temperature which is reduced over time.

4. A method according to claim 3 comprising passing the foam through a plurality of drying zones, each zone being at a different temperature, the temperature of the zones reducing from one zone to the next.

5. A method according to claim 4 comprising passing the foam through a first zone at a temperature of at least 100° C. and passing the foam through a final zone at a temperature of 50° C. or less.

6. A method according to claim 1 wherein the foam is dried at a temperature which increases and then decreases.

7. A method according to claim 1 comprising passing the foam through a first zone at a temperature of about 110–130° C. for a period of about 8–15 minutes, passing the foam through a second zone at a temperature of about 70–90° C. for a period of about 8–15 minutes and passing the foam through a third zone at a temperature of about 20–40° C. for about 8–15 minutes.

8. A method according to claim 1, wherein the pressure in the vacuum chamber is maintained below 50 mbar.

9. A method according to claim 1, wherein the drying is carried out in a belt dryer within the vacuum chamber and the method comprises evenly distributing the solution over the belt of the dryer.

10. A method of drying a lactulose solution comprising subjecting the solution to conditions of raised temperature and reduced pressure so that the solution expands into a foam, and drying the foam.

11. A method according to claim 10 wherein the foam is obtained at a temperature of at least 100° C. and a pressure no greater than 50 mbar.

* * * * *